US00PP34749P2

(12) United States Plant Patent
Ledesma

(10) Patent No.: US PP34,749 P2
(45) Date of Patent: Nov. 22, 2022

(54) MANGO TREE NAMED 'K69'

(50) Latin Name: *Mangifera indica*
Varietal Denomination: K69

(71) Applicant: Noris Ledesma, Miami, FL (US)

(72) Inventor: Noris Ledesma, Miami, FL (US)

( * ) Notice: Subject to any disclaimer, the term of this patent is extended or adjusted under 35 U.S.C. 154(b) by 0 days.

(21) Appl. No.: 17/646,185

(22) Filed: Dec. 28, 2021

(51) Int. Cl.
*A01H 5/08* (2018.01)
*A01H 6/00* (2018.01)

(52) U.S. Cl.
USPC ..... Plt./159
CPC ..... *A01H 6/00* (2018.05)

(58) Field of Classification Search
USPC ..... Plt./159
CPC ..... A01H 6/00
See application file for complete search history.

(56) References Cited

PUBLICATIONS

"The Tropical Fruit Forum", topic 'Royal Purple' mango tree, downloaded from https://tropicalfruitforum.com/index.php?topic=451.0, Feb. 23, 2012.*

The Ensey Tropical Fruit Company list of mango varieties, downloaded from enseytropicalfruit.com/new-page on Apr. 13, 2022.*

Trademark to 'Carnelian', trademark No. 97061425, filed Oct. 6, 2021.*

* cited by examiner

*Primary Examiner* — Anne Marie Grunberg

(57) ABSTRACT

A new variety of mango tree (*Mangifera indica*), 'K69' is disclosed; distinguished by production of heavy and consistent crops with large, rounded fruit averaging 1,650 g.; purpure dark, smooth to slightly undulating waxy skin, resembling a large plum with apricot aroma, peach accents and coconut and mandarin hints. Mature fruit has a striking oxblood to chrysanthemum red peel color confluent over nearly the whole surface; immature fruits are beetroot purple with an ashen, waxy sheen. Orange buff flesh, firm and melting without fiber. Flavor is sweet, rich with peach, mandarin, and coconut accents and 17.0°±1 brix. The new tree has large leaves, is vigorous and upright in growth habit with potential for commercial use and its fruit is desirable for processing due to size and quality. Leaves, bloom, and fruit have good disease tolerance. Postharvest handling rated as good but reaction to hot water treatment is unknown.

4 Drawing Sheets

Genus and species: *Mangifera indica.*
Variety denomination: 'K69'.

BACKGROUND OF THE NEW PLANT

The present invention comprises a new and distinct variety of mango tree, botanically known as *Mangifera indica*, and hereinafter referred to by the variety name 'K69'.

'K69' is a new variety of mango tree discovered as a seedling that was derived from open pollination of what was discovered as an improved seedling selection of mango tree named 'Kent' (unpatented) and was selected for remarkable qualities when compared with 'Kent'. Selection of the new variety was made on Jun. 5, 2018, at a private mango farm in the Redlands farming district of Miami-Dade County in South Florida, the United States of America and was made based on improved characteristics including disease resistance, brighter color and, large size fruit with good quality for consumption as fresh fruit and for processing. Asexual propagation of the new variety by grafting using cuttings was first performed in July 2018 using mature mango trees as topworking graft rootstock 6 years old. The propagation was done at a private mango farm in the Redlands fanning district of Miami-Dade County in South Florida, the United States of America.

The new 'K69' variety is distinguished by the production of heavy and consistent crops of fruit which are 1,650 g (58.2 oz) average weight, with a rounded base with a shallow cavity and smooth surface. The mature fruit has a red dark skin that resembles a large plum. The mature fruit has a striking oxblood to chrysanthemum red peel color confluent over nearly the whole surface. Immature fruits are purple with an ashen, waxy skin. Ripe fruit has an apricot aroma with accents of peach with a hint of coconut and mandarin. The flesh is orange, firm and without fiber. The flavor is rich and sweet and resembles a combination of peach, mandarin, and coconut with a brix of 17.0°±1. The fruit of the new 'K69' has potential for processing due its large size and quality. The tree is vigorous and upright in growth habit with large leaves. Trees in South Florida reach a height of 2.5 m (8.2 ft), a spread of 2.5 m (8.2 ft)—but with annual pruning they can be kept smaller. The leaves, bloom and fruit have good disease tolerance. Postharvest handling rated as good but reaction to hot water treatment is unknown. It has a flatted monembryonic seed with a weight average of 70 g. (2.5 oz), and 15.6 cm (6.14 in) long, 13.5 cm (5.31 in) wide and 1.01 cm (0.4 in) thick.

The new 'K69' tree has been asexually propagated via grafting using cuttings and has been found to retain its distinctive characteristics through asexual propagations.

Plant Breeder's Rights for this variety have not been applied for. The new variety 'K69' has not been made publicly available or sold anywhere in the world more than one year prior to the effective filing date of this application.

SUMMARY OF THE INVENTION

The following are the most outstanding and distinguishing characteristics of this new cultivar when grown at the Redlands farming district of Miami-Dade County in South Florida, the United States of America and can be used to distinguish 'K69' as a new and distinct variety of mango tree:

1. Excellent quality of fruit with sweet, firm, fiberless flesh and red dark skin resembling a large plum
2. Heavy and consistent crops of fruit.
3. Large fruit, resistant to anthracnose (*Colletotricum gloeosporioides*), desirable fruit for processing.

DESCRIPTION OF THE PHOTOGRAPHS

This new mango tree is illustrated by the accompanying photographs which show the entire tree, the exterior of the mature fruit and the leaves; the colors shown are as true as can be reasonably obtained by conventional photographic procedures. The photographs are of a 3-year-old tree using topworking graft rootstock 6 years old tree grown at a private mango farm in the Redlands fanning district of Miami-Dade County in South Florida, the United States of America. The pictures were taken on Jun. 17, 2021.

DESCRIPTION OF THE NEW VARIETY

Figure 1:
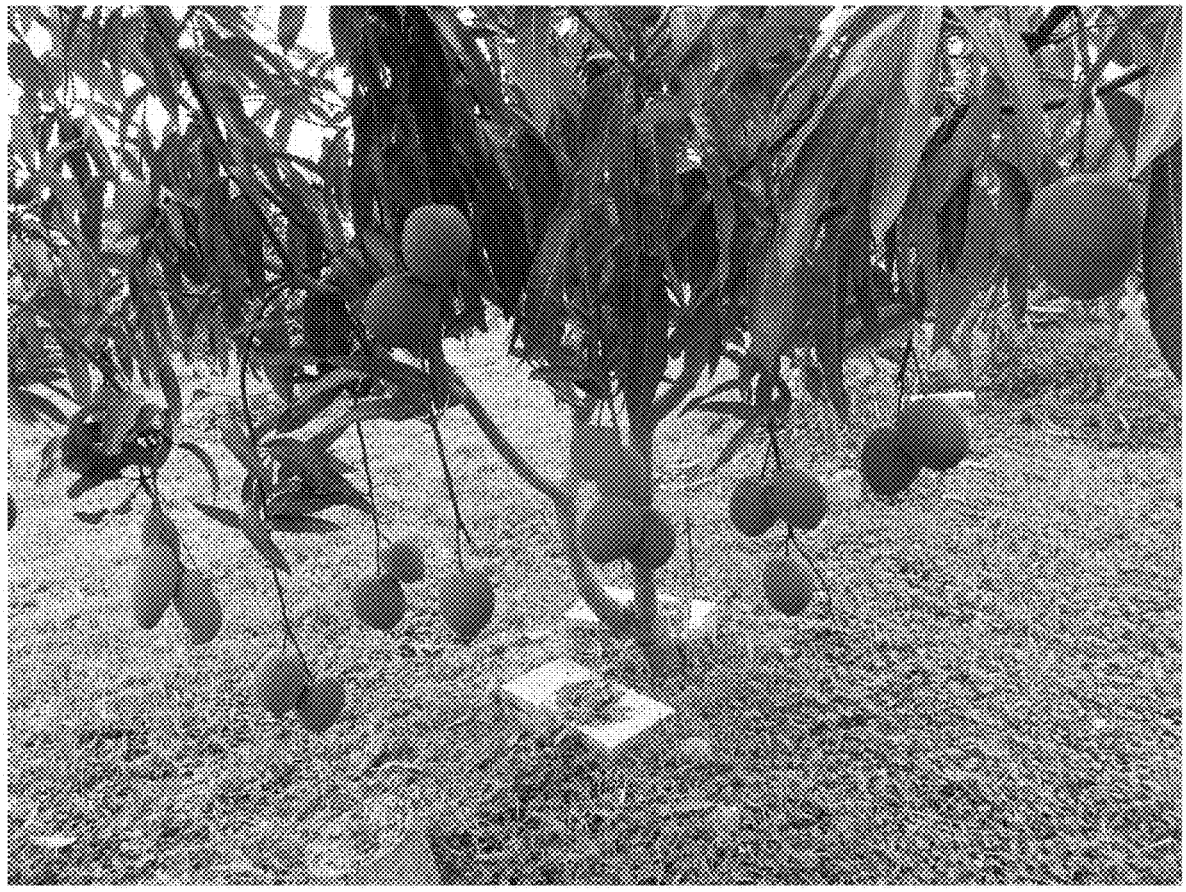
FIG. 1 shows the entire tree.
Figure 2:
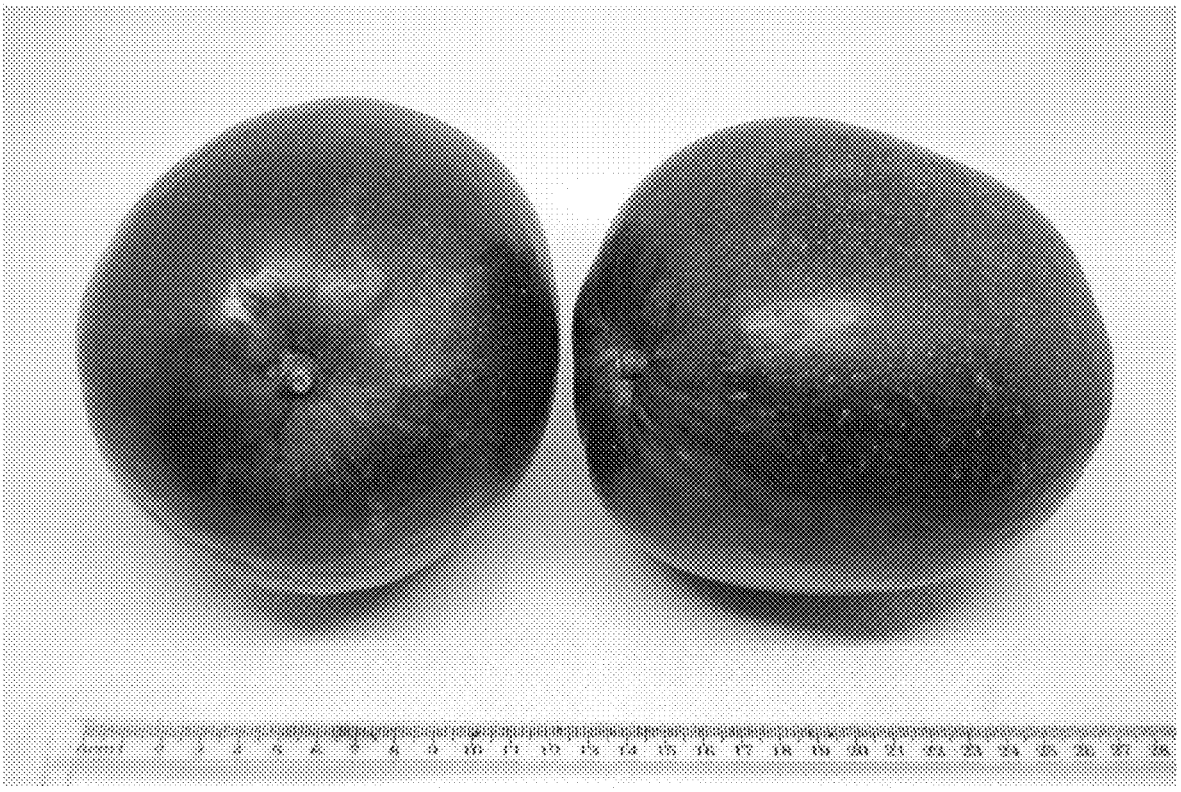
FIG. 2 shows the exterior of the mature fruit.
Figure 3:
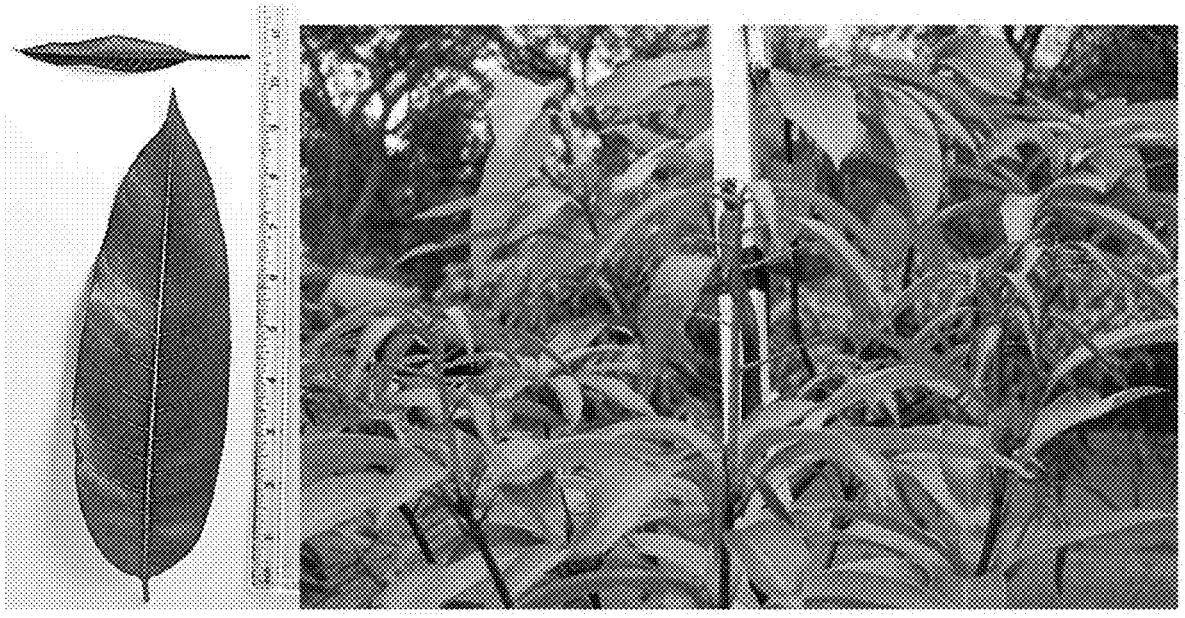
FIG. 3 shows the leaves.
Figure 4:
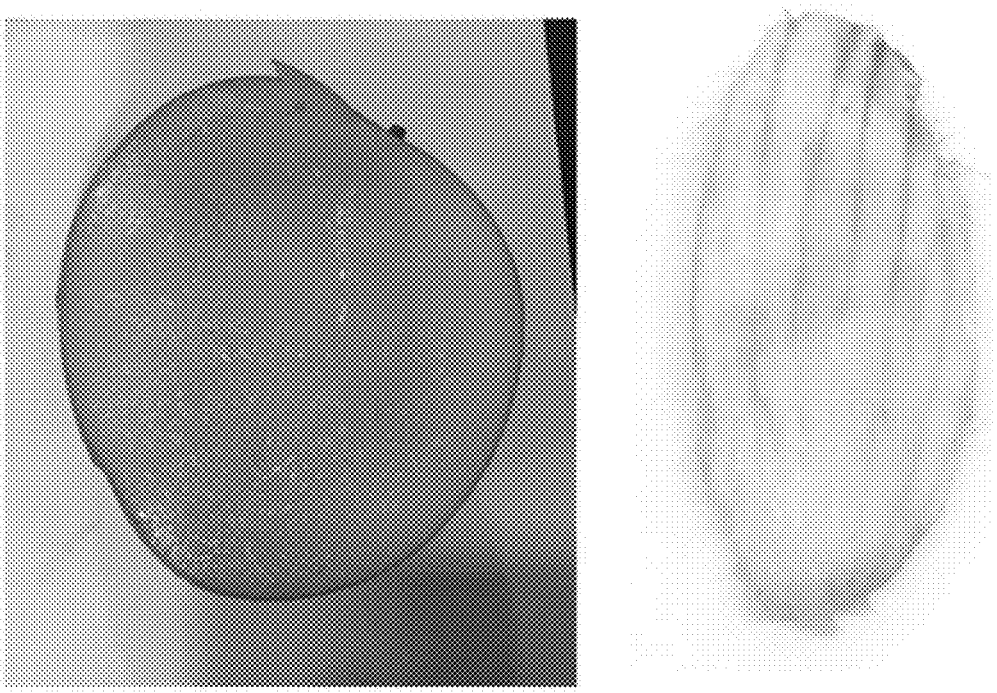
FIG. 4 shows the flesh and the stone

The following detailed descriptions set forth the distinctive characteristics of 'K69'. Trees of the new mango variety have not been observed under all possible environmental conditions. Observations and measurements were taken on a 3-year-old tree using topworking graft rootstock 6 years old tree, grown at private mango farm in the Redlands farming district of Miami-Dade County in South Florida, the United States of America.

Color readings were taken under natural light. Color references are primarily to The R.H.S. Colour Chart of The Royal Horticultural Society of London (R.H.S.) (2016 edition).

DETAILED BOTANICAL DESCRIPTION

Classification:

*Family*.—Anacardiaceae.

*Botanical name*.—*Mangifera indica*.

*Denomination*.—'K69'.

Tree:

*Growth habit*.—Vigorous and upright.

*Height*.—2.5 m (8.2 ft) high.

*Regularity of bearing*.—Regular bearing.

*Productivity*.—Very good; 49.5 kg (109.1 pound) per tree.

*Pollinator information*.—Main pollinators are flies.

Trunk:

*Diameter*.—13.0 cm (5.1 in) at 1.5 m (4.9 ft) height.

*Surface texture*.—Smooth and regular.

*Color*.—Gray to tan, consistent with trunk color of other mango varieties (approximately RHS 199B).

Branches:

*Habit*.—Spreading and open.

*Size*.—Variable.

*Surface texture*.—Smooth and regular Color (one year old and older): Same as trunk.

Leaves:

*General size*.—Large compared with other mango varieties.

*Length*.—24.0 cm (9.4 in).

*Width*.—7.5 cm (2.95 in).

*Shape*.—Lanceolate.

*Apex*.—Acute.

*Base*.—Broad angular.

*Margin*.—Smooth to slightly wavy.

*Shape in cross-section*.—Curved.

*Leaf blade twisting*.—Absent.

*Leaf blade spacing of secondary veins*.—0.5 cm (0.2 in).

*Pubescence*.—Absent.

*Color*.—Upper surface: Yellow Green (RHS 146B). Lower surface: Typically, the same as upper (Yellow green), or with a slightly more yellow tint (RHS 146C). Color (immature): Greyed purple (RHS 187A).

*Petiole*.—Erect in relation to shoot. Length: 1.8 cm to 2.6 cm (0.7 in to 1.02 in). Diameter: 0.4 cm to 0.5 cm (0.16 in to 0.20 in). Color (mature): Gray (RHS 201A). Color (immature): Brown to wine (RHS 177A).

Inflorescence:

*General*.—Flowers produced on terminal inflorescences with thousands of individual flowers. Inflorescence is pyramidal, 43 cm (16.9 in) long and 28 cm (11 in) diameter at the base, with dense flowering.

*Date of bloom*.—Early-December to early March.

Flower bud:

*Length*.—2.6 mm (0.102 in).

*Surface texture*.—Surface is firm.

Flowers: Petals and sepals: Both male and hermaphrodite flowers have 5 petals and sepals. The flowers are produced on terminal inflorescences and have high percentage of hermaphrodite flowers (52% to 72%) compared with other cultivars, under South Florida conditions. Male flowers are a pale cream color (RHS 155B) with yellow in the center (RHS 154-4B). Flowers have good tolerance to anthracnose (*Colletotricum gloeosporioides*) and moderate susceptibility to powdery mildew (*Oidium mangiferae*).

Reproductive organs:

*Anther quantity*.—5 per flower.

*Anther color*.—White (RHS 155B).

*Ovary quantity*.—1.

Fruit: General: The fruit are ripe for commercial harvesting and shipment approximately June through July in the Redlands farming district of Miami-Dade County in South Florida, the United States of America.

The fruit are large, Length: Typical average length: 16.8 cm (6.6 in); Diameter: Typical average diameter: 15.5 cm (6.1 in); Thickness: 13.2 cm (5.20 in); Weight: Typical average weight: 1,650 g (58.2 oz). Shape: Oblong to oval, Shape of fruit apex: round, Depth of fruit cavity: shallow, Fruit neck prominence: Absent, Fruit beak: Absent. The shape of the ventral shoulder of mature fruit: Rounded ending in a long curve, Groove in the ventral shoulder: Absent. Bulging on the ventral shoulder: absent, Fruit sinus: Absent. Stylar scar: Absent. Fruit skin surface: Slightly wavy; Fruit skin surface texture: Smooth, Density of lenticels: Sparse, Lenticels color: yellow (RHS 162C), Fruit skin waxiness: Waxy. Color fruit: Immature fruit turn beetroot purple with waxy sheen (RHS 59A), and when they ripe fruit turned brilliant oxblood to chrysanthemum red peel color (RHS 45 B) confluent over nearly the whole surface. Flesh: Texture: Firm, melting, and juicy without fiber; Color: Yellow Orange (RHS 23A). Flavor: Excellent flavor reminiscent of peach, mandarin, and coconut with a brix of 17.0°±1. Fragrance: peach with a hint of coconut and mandarin. Softening: Time to softening (ripening) depends on stage of maturity (3 to 10 days); softening is uniform and rapid once it begins yet flesh firmness is maintained for several days at room temperature. Use: Mango pulp and juice, keeping quality: Above average shipping and shelf life, Harvesting: By hand. Fruit stalk attachment: Strong, Peduncle: Hard, cylindrical; Length: 13.5 cm (5.3 in) to 16.0 cm (6.30 in); Diameter: 0.4 cm (0.16 in); Color: Brown to gray (RHS 199B). Seed: Stone shape: Flatted, oblong-oval, weight average of 70 gr (2.5 oz), Length: 15.6 cm (6.14 in); Breadth: 13.5 cm (5.31 in); Thickness: 1.01 cm (0.4 in), Texture: Thick and woody; tied to the pulp; Color: White 58D; Veins on stone: level with surface; pattern of stone venation: parallel; quantity of fibers on stone: low. Embryo: Monoembryonic; Embryo Color: White 155A, shape: oblong.

Disease resistance: Anthracnose (*Colletotricum gloeosporioides*): Good tolerance; Powdery mildew (*Oidium mangiferae*): Moderate susceptibility.

Physiological conditions: Sap burn is not a problem.

The new 'K69' variety differs from the parent tree 'Kent' (unpatented) in that 'K69' produces fruit that are uniform in shape where most fruit are oblong to oval with a rounded base and shallow cavity with an average weight of 1,650 g (58.2 oz). Immature fruits are beetroot purple with an ashen, waxy sheen, and when ripen turned to a striking oxblood to chrysanthemum red peel color confluent over nearly the whole surface. The tree is large, and vigorous with an upright growth habit, it has large leaves, and it is highly productive, with good disease tolerance. 'Kent' produces fruit average 600 g (21.2 oz) that varies in shape where some are more elongated and some are rounded, and the base color is green with yellow and some red blush. Additionally, the tree is vigorous, large, and compact canopy and heavily susceptible to Anthracnose (*Colletotricum gloeosporioides*) when grown under the same environmental conditions in the Redlands farming district of Miami-Dade County in South Florida, the United States of America.

'K69' differs from commercial mango variety 'Haden' (unpatented) in that 'K69' produces large fruit with red peel over the whole surface and is resistant to Anthracnose (*Colletotricum gloeosporioides*) whereas 'Haden' has bright yellow skin, with red blush, and numerous yellow dots and highly susceptible to Anthracnose (*Colletotricum gloeosporioides*) which make it a disadvantage for fruit processing.

The invention claimed is:

1. The invention of a new and distinct mango tree named, 'K69' as herein illustrated and described, having an excellent quality of fruit with a striking oxblood to chrysanthemum red peel color confluent over nearly the whole surface, rich and sweet flavor resembling a combination of peach, mandaring and coconut, large fruit weighting an average of 1,650 g. desirable for fruit processing and, excellent disease tolerance.

* * * * *